(12) United States Patent
Sakuma et al.

(10) Patent No.: US 7,772,855 B2
(45) Date of Patent: Aug. 10, 2010

(54) INSTRUMENT FOR MEASURING CONCENTRATION OF PARTICULATES IN FLUID, MEASURING METHOD, AND MEASURING PROGRAM

(75) Inventors: Takeshi Sakuma, Nagoya (JP); Kyosuke Katsuyama, Nagoya (JP); Kenshin Kitoh, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 12/506,591

(22) Filed: Jul. 21, 2009

(65) Prior Publication Data

US 2009/0284271 A1 Nov. 19, 2009

Related U.S. Application Data

(63) Continuation of application No. PCT/JP2008/052134, filed on Feb. 8, 2008.

(30) Foreign Application Priority Data

Feb. 9, 2007 (JP) ............... 2007-031060

(51) Int. Cl.
*G01N 15/06* (2006.01)
*G01R 27/08* (2006.01)

(52) U.S. Cl. ............ 324/693; 324/71.4; 73/53.04
(58) Field of Classification Search .......... 324/693, 324/71.4; 73/53.04
See application file for complete search history.

(56) References Cited

U.S. PATENT DOCUMENTS 4,656,832 A 4/1987 Yukihisa et al.
4,686,453 A 8/1987 Kato et al.
5,968,371 A * 10/1999 Verdegan et al. ............ 210/739
7,096,855 B2 * 8/2006 Renner et al. ............... 123/494
7,261,008 B2 * 8/2007 Saaski et al. ............. 73/863.22
7,299,682 B2 * 11/2007 Boyle et al. ................ 73/53.05
2003/0070423 A1 * 4/2003 Morinaga et al. ............ 60/284
2008/0048681 A1 2/2008 Birkhofer et al.
2009/0140754 A1 * 6/2009 Schenkl et al. ............. 324/693

FOREIGN PATENT DOCUMENTS

| EP | 0 675 267 A1 | 10/1995 |
| JP | 58-143816 A1 | 8/1983 |
| JP | 59-060018 A1 | 4/1984 |
| JP | 61-111450 A1 | 5/1986 |
| JP | 04-203413 A1 | 7/1992 |
| JP | 07-270296 A1 | 10/1995 |
| JP | 08-261904 A1 | 10/1996 |
| WO | 2005/093233 A1 | 10/2005 |

* cited by examiner

*Primary Examiner*—Timothy J Dole
*Assistant Examiner*—John Zhu
(74) *Attorney, Agent, or Firm*—Burr & Brown

(57) ABSTRACT

There are disclosed an instrument for measuring the concentration of particulates in a fluid, which is capable of determining the concentration of the particulates in the fluid with high accuracy. The instrument for measuring the concentration of the particulates in the fluid includes particulate collecting means, temperature measuring means, flow rate measuring means, impedance measuring means, time measuring means, constant determining means for determining an impedance change per unit time-particulate concentration constant from temperature and flow rate, impedance change per unit time computing means for computing the change of an impedance per unit time, and particulate concentration determining means for determining the concentration of the particulates from the change of the impedance per unit time computed by the impedance change per unit time computing means.

3 Claims, 3 Drawing Sheets

INSTRUMENT FOR MEASURING CONCENTRATION OF PARTICULATES IN FLUID, MEASURING METHOD, AND MEASURING PROGRAM

TECHNICAL FIELD

The present invention relates to an instrument for measuring the concentration of particulates in a fluid, a method for measuring the concentration of particulates in a fluid, and a program for measuring the concentration of particulates in a fluid.

BACKGROUND ART

Regulations on the emission of harmful substances included in an exhaust gas from a car have been more and more strict, and it is considered in the U.S. that a car-mounted diagnosis device of the emission will be essential in 2010.

Moreover, it is also reported that even a gasoline vehicle discharges a larger amount of particulates (a particulate matter (PM)) than a diesel vehicle on which a particulate collecting filter (DPF) is mounted, in a case where the gasoline vehicle has a system for directly jetting a fuel into a cylinder.

In Patent Document 1, it is noted that particulates included in the exhaust gas are made of particulates having conductivity, and there are disclosed a particulate detection device and a particulate detection filter utilizing a fact that the electric resistance of an electric insulating member decreases, when the conductive particulates are attached to or adsorbed by the member.

Moreover, in Patent Document 2, a technology is disclosed in which light emitted from a light source is transmitted through the flow of the exhaust gas and received by a light receiving portion, and the light impermeability of the exhaust gas having a constant correlation function between the gas and the concentration of the particulates is detected, whereby the impermeability is converted into the concentration of the particulates by control means.

Patent Document 1: JP-A-59-060018
Patent Document 2: JP-A-04-203413

DISCLOSURE OF THE INVENTION

At present, however, there have not been suggested a sufficient instrument for measuring the concentration of particulates in a fluid, a method for measuring the concentration of particulates in a fluid and a program for measuring the concentration of particulates in a fluid.

According to the invention disclosed in Patent Document 1, the amount of the particulates collected by a filter can be measured, but the amount of the particulates included in a gas flow cannot be measured.

Moreover, in a method for transmitting light through an exhaust gas tube to measure the impermeability of the light as in the invention disclosed in Patent Document 2, the whole exhaust gas flow can be measured, but there is a problem that accuracy gradually deteriorates because windows of light emitting and receiving portions become dirty.

The present invention has been developed in view of the problems of such a conventional technology, and an object thereof is to provide an instrument for measuring the concentration of particulates in a fluid, which is capable of determining the concentration of the particulates in the fluid with high accuracy, without being influenced by the amount of the particulates deposited on a detector, a method for measuring the concentration of particulates in a fluid, and a program for measuring the concentration of particulates in a fluid.

The present inventors have intensively performed investigations for achieving the above object, and have eventually found that (1) there is a correlation between the amount of the particulates deposited on particulate collecting means and the change of the impedance of the particulate collecting means, (2) the amount of the particulates collected by the particulate collecting means is influenced by the flow rate of the fluid and (3) when a temperature and the flow rate are constant, there is a correlation between the concentration of the particulates in the fluid and the change of the impedance of the particulate collecting means per unit time, whereby the present invention has been completed.

That is, according to the present invention, an instrument for measuring the concentration of particulates in a fluid, a method for measuring the concentration of particulates in a fluid and a program for measuring the concentration of particulates in a fluid are provided as follows.

[1] An instrument for measuring the concentration of particulates in a fluid, including: particulate collecting means for collecting the particulates in the fluid; temperature measuring means for measuring the temperature of the particulate collecting means; flow rate measuring means for measuring the flow rate of the fluid passing through the particulate collecting means; impedance measuring means for measuring the impedance of the particulate collecting means; and information processing means, wherein the information processing means includes time measuring means for measuring the elapse of time, constant determining means for determining an impedance change per unit time-particulate concentration constant from input temperature and flow rate, impedance change per unit time computing means for computing the change of the input impedance per unit time measured by the time measuring means, and particulate concentration determining means for determining the concentration of the particulates from the change of the impedance per unit time computed by the impedance change per unit time computing means by use of the impedance change per unit time-particulate concentration constant determined by the constant determining means.

[2] A method for measuring the concentration of particulates in a fluid, including the steps of: measuring the temperature, flow rate and impedance of particulate collecting means for collecting the particulates in the fluid; determining an impedance change per unit time-particulate concentration constant from the measured temperature and flow rate; computing the change of the measured impedance per unit time; and determining the concentration of the particulates from the computed change of the impedance per unit time by use of the determined impedance change per unit time-particulate concentration constant.

[3] A program for measuring the concentration of particulates in a fluid, which allows a computer to accept the input of temperature, flow rate and impedance, determine an impedance change per unit time-particulate concentration constant from the accepted temperature and flow rate, compute the change of the input impedance per unit time, and determine the concentration of the particulates from the computed change of the impedance per unit time by use of the determined impedance change per unit time-particulate concentration constant.

According to the present invention, there are provided an instrument for measuring the concentration of particulates in a fluid, which is capable of determining the concentration of the particulates in the fluid at low cost and with high accuracy, without being influenced by the amount of the particulates deposited on a detector, a method for measuring the concentration of particulates in a fluid, and a program for measuring the concentration of particulates in a fluid.

DESCRIPTION OF REFERENCE NUMERALS

10: particulate collecting means, 20: temperature measuring means, 30: flow rate measuring means, 40: impedance measuring means, 50: information processing means, 60: display means, 70: printing means, 80: communication means, 100: central processing means, 110: time measuring means, 120: constant determining means, 130: impedance change per unit time computing means, 140: particulate concentration determining means, 200: storage means, and 210: table.

BEST MODE FOR CARRYING OUT THE INVENTION

Hereinafter, the best mode for carrying out the present invention will be described, but it should be understood that the present invention is not limited to the following embodiment and that the present invention includes the appropriate alteration, improvement and the like of the following embodiment based on the ordinary knowledge of a person with ordinary skill without departing from the scope of the present invention.

Figure 1:
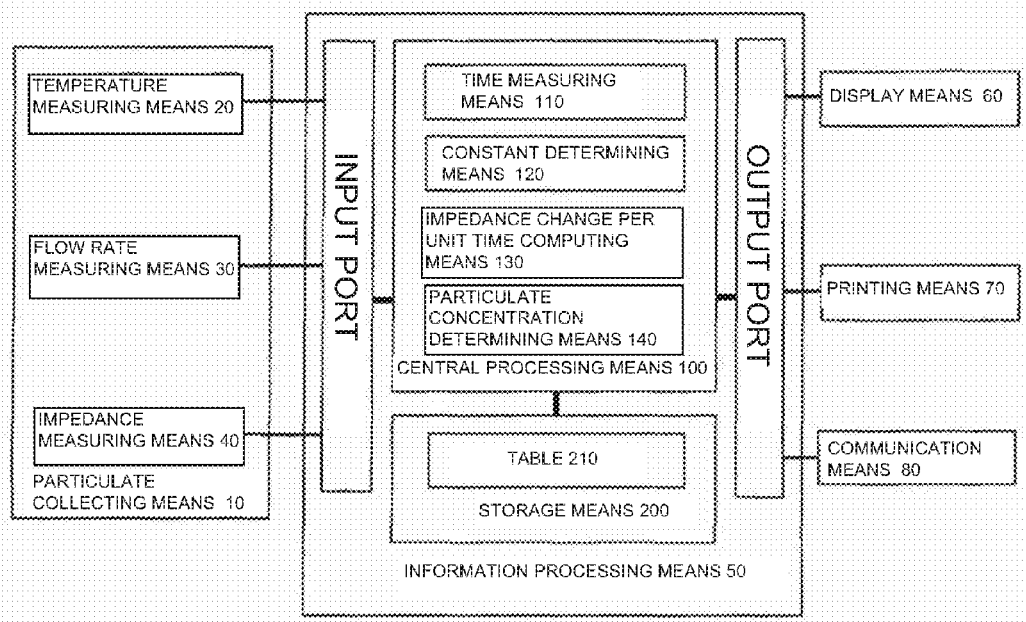
FIG. 1 is a function block diagram showing one embodiment of the present invention.

The present invention will be described with reference to the drawings. FIG. 1 is a function block diagram showing one embodiment of the present invention. Particulate collecting means 10 is disposed in a through channel of a fluid (not shown). This particulate collecting means 10 is provided with temperature measuring means 20, flow rate measuring means 30 and impedance measuring means 40. The temperature measuring means 20, the flow rate measuring means 30 and the impedance measuring means 40 are connected to an input port of information processing means 50. It is to be noted that when the temperature measuring means 20, the flow rate measuring means 30 and the impedance measuring means 40 are not directly connected to the input port of the information processing means 50, data having a correlation with respect to temperature and flow rate in the particulate collecting means 10 may be acquired and used from another measurement instrument or the like by communication.

The information processing means 50 is connected to the temperature measuring means 20, the flow rate measuring means 30 and the impedance measuring means 40 via the input port, and is also connected to display means 60, printing means 70 and communication means 80 via an output port. The information processing means 50 includes central processing means 100 and storage means 200 in addition to the input port and the output port.

The central processing means 100 is connected to the input port, the output port and the storage means 200. Moreover, the central processing means 100 includes time measuring means 110. Furthermore, the central processing means 100 reads a program stored in the storage means 200 to function as constant determining means 120, impedance change per unit time computing means 130 and particulate concentration determining means 140.

The storage means 200 is connected to the central processing means 100. Moreover, in the storage means 200, a program for causing the central processing means 100 to function as respective means, parameters, tables and the like are stored. In addition, the storage means secures a region for storing data measured by the respective measuring means, data computed as a result of data processing by the central processing means 100 and the like. Moreover, the storage means 200 stores a table 210 in which an impedance change per unit time-particulate concentration constant at each temperature and each flow rate is recorded.

The display means 60, the printing means 70 and the communication means 80 are connected to the output port of the information processing means 50, respectively.

Next, the function of the embodiment of the present invention shown in the function block diagram of FIG. 1 will be described. When the fluid including particulates flows through the through channel of the fluid (not shown), the particulates are collected by the particulate collecting means 10 disposed in the fluid through channel (not shown). The temperature and impedance of the particulate collecting means 10 and the flow rate of the fluid passing through the particulate collecting means are measured by the temperature measuring means 20, the impedance measuring means 40 and the flow rate measuring means 30, respectively. The information processing means 50 accepts these measurement data, and performs predetermined processing as described later. Moreover, a program for measuring the concentration of the particulates in the present invention allows a computer as the information processing means 50 to perform the predetermined processing described hereinafter.

As described later in detail, the present inventors have found that there is a correlation between the amount of the particulates deposited on the particulate collecting means and the change of the impedance of the particulate collecting means and that when the temperature and the flow rate are constant, there is a correlation between the concentration of the particulates in the fluid and the change of the impedance of the particulate collecting means. Moreover, the impedance changes depending on the temperature. Therefore, when an impedance change per unit time-particulate concentration constant at each temperature and flow rate is obtained in advance, the impedance change of the particulate collecting means can be observed to obtain the concentration of the particulates in the fluid.

The constant determining means 120 determines the impedance change per unit time-particulate concentration constant from the temperature input from the temperature measuring means 20 to the information processing means 50 and the flow rate input from the flow rate measuring means 30 to the information processing means 50. Specifically, the impedance change per unit time-particulate concentration constant at each temperature and flow rate is obtained in advance by experiment, calculation or the like, and stored as the table 210 in the storage means 200. When this table 210 is used, the impedance change per unit time-particulate concentration constant is uniquely determined from the temperature and flow rate. When the temperature and flow rate are input, the constant determining means 120 calls the table 210 from the storage means 200, and takes the impedance change per unit time-particulate concentration constant specified by the input temperature and flow rate.

The impedance change per unit time computing means 130 computes the change of the impedance input from the impedance measuring means 40, per unit time measured by the time measuring means 110. Specifically, the impedance change per unit time computing means 130 specifies the impedance input from the impedance measuring means 40 continuously at an arbitrary time point. Next, the impedance change per unit time computing means 130 allows the time measuring means 110 to start the time measurement. When the time measuring means 110 measures the elapse of the unit time, the impedance change per unit time computing means 130 again specifies the impedance input from the impedance measuring means 40 continuously. The impedance change per unit time computing means 130 computes the change of the impedance per unit time from a difference between these impedances.

The particulate concentration determining means 140 determines the concentration of the particulates from the change of the impedance per unit time computed by the impedance change per unit time computing means 130, by use of the impedance change per unit time-particulate concentration constant determined by the constant determining means 120. Specifically, the particulate concentration determining means 140 computes the product of the inverse number of the impedance change per unit time-particulate concentration constant and the change of the impedance per unit time to determine the concentration of the particulates.

The present invention has been described above with respect to FIG. 1, but the present invention is not limited to this embodiment. For example, an embodiment has been described above in which the impedance change-particulate concentration constant at each temperature and flow rate is prepared as the table 210, but the present invention is not limited to this embodiment. An appropriate curve at each temperature or flow rate may be obtained in advance from experiment data or the like, and values may be applied to this curve to determine the impedance change-particulate concentration constant. Moreover, an embodiment for continuously measuring the impedance has been described above, but the present invention is not limited to this embodiment. The impedance may be measured every time the elapse of a predetermined time is measured by the time measuring means 110.

Furthermore, there has been described above an embodiment in which the temperature measuring means 20 and the flow rate measuring means 30 are arranged in the particulate collecting means 10, but the present invention is not limited to this embodiment. In short, there is not any special restriction on the means as long as the temperature in the particulate collecting means 10 and the flow rate of the fluid passing through the particulate collecting means 10 can be measured, and the means may be arranged before or after the particulate collecting means 10. Moreover, there has been described above an embodiment in which the temperature measuring means 20, the flow rate measuring means 30 and the impedance measuring means 40 are directly connected to the input port of the information processing means 50, but these measuring means may be connected to the input port of the information processing means via another means. For example, the temperature measuring means 20 and the flow rate measuring means 30 are connected to second information processing means (not shown), and the means may be connected to the information processing means 50 via the second information processing means.

[Particulate Collecting Means]

In the present invention, the particulate collecting means is means capable of collecting the particulates in the fluid. The particulate collecting means in the present invention does not have to collect all the particulates passing through the fluid. However, a part of the passing particulates has to be collected. Examples of the particulate collecting means usable in the present invention include a honeycomb structure as a structure having a large number of through channels (cells) partitioned by partition walls and extending through the structure in an axial direction; a particulate collecting filter (DPF) in which the ends of predetermined cells on one side are plugged by plugging portions made of a plugging material charged into the cells and in which the ends of the remaining cells on a side opposite to the ends of the predetermined cells are similarly plugged by plugging portions; and Cerafoam in which a pore former such as foam polyurethane is mixed, kneaded and fired with a ceramic clay so that the porosity of the resultant formed article is 75% or more, but the present invention is not limited to these examples.

[Temperature Measuring Means]

The temperature measuring means in the present invention is means capable of measuring the temperature of the particulate collecting means. Examples of the temperature measuring means usable in the present invention include a thermocouple, a platinum resistor and a thermister, but the present invention is not limited to these examples. High accuracy is not required, but means having good time response is preferable.

[Flow Rate Measuring Means]

In the present invention, the flow rate measuring means is means capable of measuring the flow rate of the fluid passing through the particulate collecting means. Examples of the flow rate measuring means usable in the present invention include a heat type gas flow rate meter and a differential pressure type meter, but the present invention is not limited to these examples.

[Impedance Measuring Means]

In the present invention, the impedance measuring means is means capable of measuring the impedance of the particulate collecting means. Examples of the impedance measuring means usable in the present invention include a direct current resistance meter and an LCR meter capable of measuring an alternate current resistance or the like, but the present invention is not limited to these examples. However, the means preferably has a performance capable of measuring a high resistance in a measurement range up to several tens of $M\Omega$. When the particulate collecting means is the honeycomb structure, the DPF or Cerafoam, a pair of electrodes may be arranged in a portion of the honeycomb structure for collecting the particulates, and an alternate current is applied between the electrodes, whereby the impedance can be measured.

[Information Processing Means]

As the information processing means in the present invention, a widespread computer may be employed.

[Communication Means]

As the communication means in the present invention, widespread wired or wireless means may be employed. In the present invention, data obtained by each means, data processed by the information processing means 50 or the like can be transmitted to another device or the like via the communication means. In the present invention, the temperature measuring means 20, the flow rate measuring means 30 and the impedance measuring means 40 may acquire data measured by another ECU or the like by communication with the ECU or the like and use the data as the temperature, flow rate and impedance. A communication signal may be either analog data or digital data, but it is preferable to transport the digital data in consideration of widespread car-mounted data communication CAN. When the particulate concentration measuring instrument of the present invention is disposed in an exhaust gas passage of a car, the present concentration of the particulates in the exhaust gas can be transmitted to the electronic control unit (ECU) or the like via the communication means in real time. It is to be noted that if the communication means is unnecessary in the present invention, the means may be omitted.

[Display Means]

As the display means in the present invention, a widespread display device such as a liquid crystal display, a CRT display, an EL display or a plasma display may be employed. When the particulate concentration measuring instrument of the present invention is disposed in the exhaust gas passage of the car, the display means can display numeric values, graphs or the like in order to inform a driver or the like of the present concentration of the particulates in the exhaust gas in real time. It is to be noted that if the display means is unnecessary in the present invention, the means may be omitted.

REFERENCE EXAMPLE

To a cordierite forming material prepared by mixing powder of talc, kaolin, calcinated kaolin, alumina, aluminum hydroxide and silica at a predetermined ratio in a range of a chemical composition including 42 to 56 mass % of $SiO_2$, 0 to 45 mass % of $Al_2O_3$ and 12 to 16 mass % of MgO, 15 to 25 mass % of graphite as a pore former, and 5 to 15 mass % of a synthetic resin such as PET PMA, or a phenol resin in total were added. Furthermore, the predetermined amounts of methyl celluloses and a surfactant were added, and water was added to and kneaded with the resultant mixture to form a kneaded clay. Next, this clay was vacuum-deaerated, and then extruded to form a honeycomb structure. The structure was dried by a microwave drying process and a hot air drying process, and fired at a maximum temperature of 1400 to 1435° C. to manufacture the honeycomb structure made of a porous ceramic material (cordierite). Two portions of the outer peripheral surface of this honeycomb structure were coated with a silver paste and baked, to form electrodes. Next, the structure was connected to an impedance measuring circuit for measuring an alternate current impedance between the electrodes. This honeycomb structure provided with the electrodes was received in a can member together with a particulate collecting filter.

Experiment 1

Figure 2:
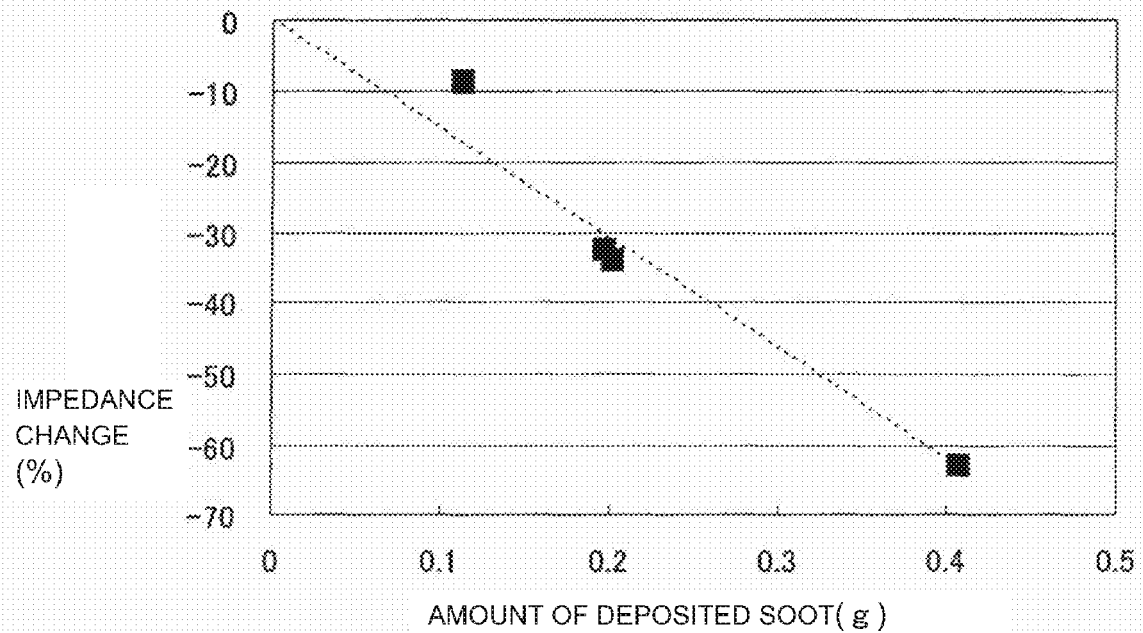
FIG. 2 is a diagram showing a relation between the amount of deposited particulates and the change of an impedance.

Relation Between Amount of Particulates Deposited on Particulate Collecting Means and Change of Impedance A diesel engine exhaust gas including particulates (soot) was caused to flow through the can member, and the alternate current impedance between the electrodes was measured while depositing the particulates on the honeycomb structure provided with the electrodes, whereby a relation between the mass of the deposited particulates and the change ratio of the measured alternate current impedance was obtained as shown in FIG. 2. Engine conditions were set so that the rotation number and torque of a diesel engine having a 2 L displacement were 1500 rpm/50 Nm, and an open degree was 50% of that of an EGR valve. Exhaust gas conditions at this time were 220° C., 1.3 $Nm^3$/min and a particulate concentration of 0.8 g/hr. It is seen from FIG. 2 that there is a correlation between the amount of the particulates deposited on the particulate collecting means and the change of the impedance.

Experiment 2

Figure 3:
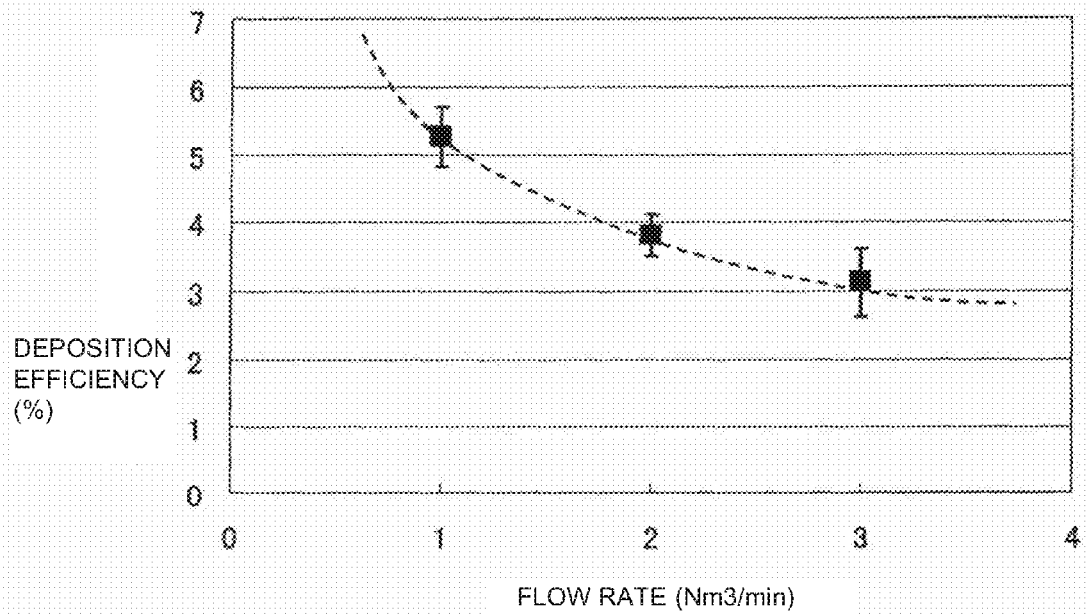
FIG. 3 is a diagram showing a relation between the amount of the deposited particulates and a flow rate.

Relation Between Amount of Particulates Deposited on Particulate Collecting Means and Flow Rate of Fluid A burner combustion gas simulating the diesel engine exhaust gas including the particulates were caused to flow while changing the flow rate by use of the above can member, whereby the particulates were deposited on the honeycomb structure provided with the electrodes. The amount of the collected particulates was obtained from a weight difference between the honeycomb structures before and after a test. Results are shown in FIG. 3. The test was conducted on conditions including a gas temperature of 200° C., a particulate concentration of 2.0 to 2.4 g/hr and a flow rate of 1, 2, 3 $Nm^3$/min. It is seen from the diagram that there is a correlation between the amount of the collected particulates and the flow rate.

Experiment 3

Relation Between Particulate Concentration and Impedance Change

Figure 4:
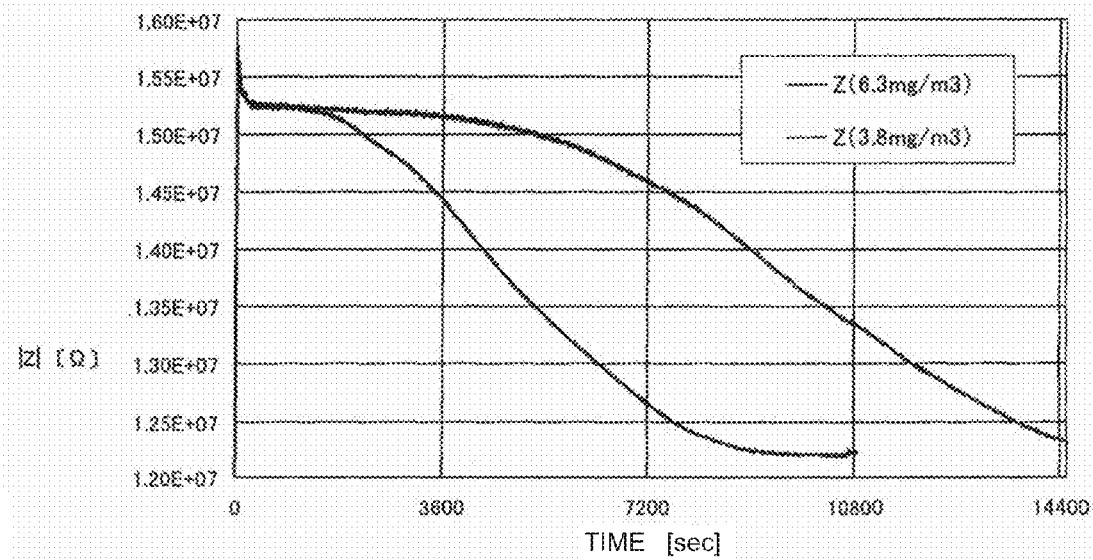
FIG. 4 is a diagram showing a relation between the concentration of the particulates in a fluid and the flow rate.
Figure 5:
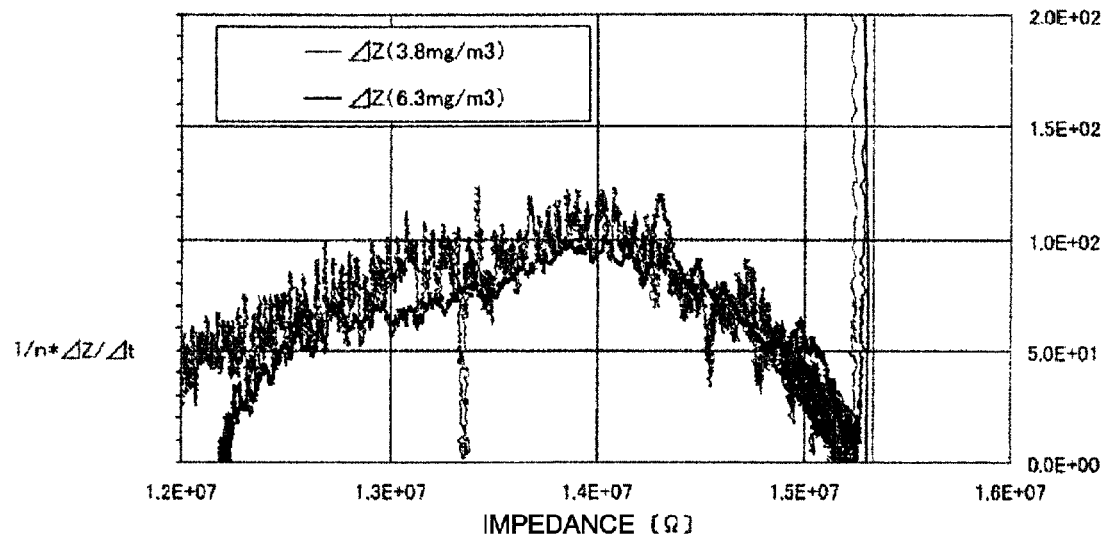
FIG. 5 is a diagram showing a relation between the product of the inverse number of the concentration of the particulates in the fluid and the impedance change and the impedance.

The diesel engine exhaust gas including the particulates (the soot) having a predetermined concentration was caused to flow through a can member similar to the above can member, and the alternate current impedance between the electrodes was measured while depositing the particulates on the honeycomb structure provided with the electrodes in the same manner as described above, except that to improve an impedance detection sensitivity, one end surface of the above honeycomb structure was bored in a spherical shape so that the center of the end surface was dented most, and the structure was received in the can member so that the end surface was positioned between the electrodes and so that the bored end surface was positioned on the side of the particulate collecting filter. A relation between an elapsed time and the impedance was obtained as shown in FIG. 4. An exhaust gas flow rate was set to 1.3 $Nm^3$/min., an exhaust gas temperature was set to about 220° C., and the concentration of the discharged particulates was set to 3.8 $mg/m^3$ and 6.3 $mg/m^3$. As test conditions at 3.8 $mg/m^3$, the rotation number and torque of the diesel engine having the 2 L displacement were set to 1650 rpm/55 Nm, and the open degree was 29% of that of the EGR valve. Moreover, as test conditions at 6.3 $mg/m^3$, the rotation number and torque of the same engine were set to 1500 rpm/60 Nm, and the open degree was 50% of that of the EGR valve. A relation between the product of the inverse number of the particulate concentration and the impedance change and the impedance was obtained as shown in FIG. 5. It is seen from FIG. 5 that a(Z) is substantially equal, even when the particulate concentration varies.

A relation of equation (1) is derived from FIG. 4.

$\Delta Z/\Delta t \propto n$ (particulate concentration) (1), in which Z is impedance, t is time and n is the particulate concentration.

$\Delta Z/\Delta t$ changes in accordance with the impedance Z, and hence a relation of equation (2) is established.

$a(Z)=(1/n)\times\Delta Z/\Delta t$ (2), in which $a(Z)$ is an impedance change per unit time-particulate concentration constant.

When $a(Z)$ is obtained by an experiment or the like, the particulate concentration can be obtained from equation (3).

$$n=1/a(Z)\times\Delta Z/\Delta t \quad (3).$$

$a(Z)$ is the impedance change per unit time-particulate concentration constant at each impedance, but needless to say, $a(\Delta Z)$ may be represented as the impedance change-particulate concentration constant at an impedance change amount $\Delta Z$ from an initial value $Z0$.

EXAMPLES

Hereinafter, the present invention will specifically be described in accordance with examples, but the present invention is not limited to these examples.

A diesel engine exhaust gas including particulates (soot) was caused to flow through the above can member while changing the concentration of particulates. An exhaust gas temperature measured by a thermocouple as temperature measuring means was 220° C., and a flow rate measured by a flow rate sensor as flow rate measuring means was 1.3 m³/min at 25° C. An impedance change-particulate concentration constant at an impedance change amount $\Delta Z$ from an initial value $Z0$, determined from this temperature and the flow rate, was obtained as shown in equation (4).

$$a(\Delta Z)=-1.00\times10^{-15}\times\Delta Z^3+6.17\times10^{-9}\times\Delta Z^2-1\times10^{-2}\times\Delta Z \quad (4).$$

Figure 6:
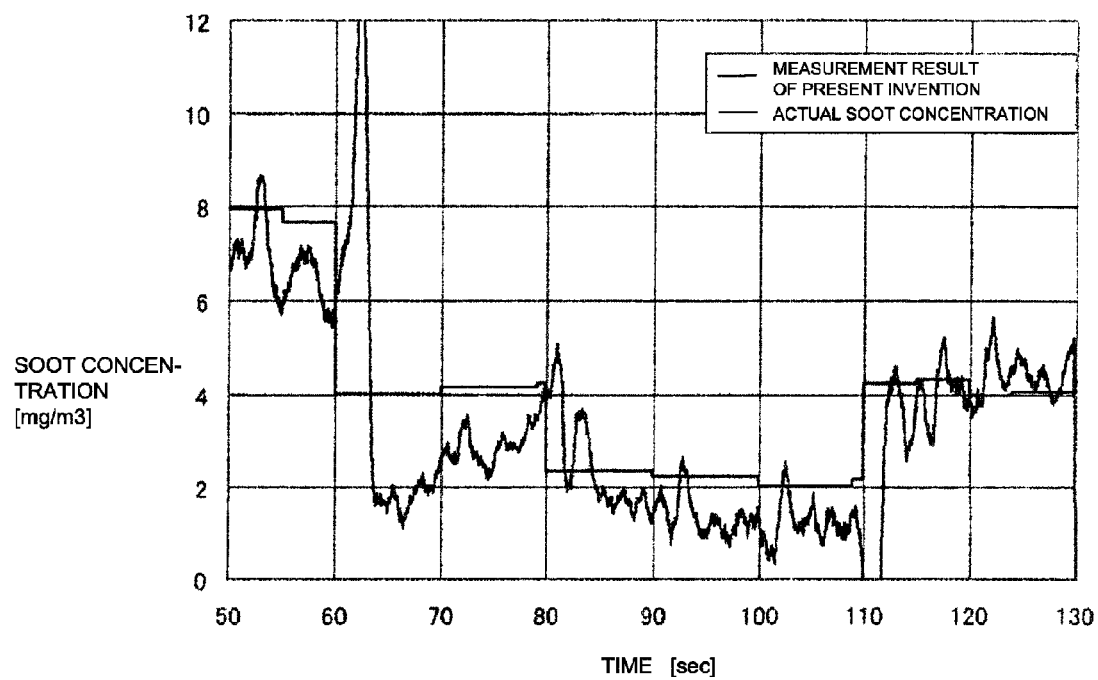
FIG. 6 is a diagram showing the concentration of the particulates (soot) measured by a particulate concentration measuring instrument of the present invention and a smoke meter.

The particulate (soot) concentration obtained from the measurement result of the impedance is shown in FIG. 6.

Moreover, at this time, the particulate (soot) concentration was measured by a smoke meter manufactured by AVL CO., Ltd. for measuring a soot and smoke concentration by use of a shielding function of the soot and smoke in a discharged gas. The results are shown in FIG. 6. It is seen from FIG. 6 that the concentration of the particulates in the fluid obtained by the particulate concentration measuring instrument and measuring method of the present invention well matches the concentration of the particulates measured by the smoke meter.

INDUSTRIAL APPLICABILITY

The present invention can be used for measuring the amount of particulates discharged from an exhaust system of an internal combustion engine or the like.

The invention claimed is:

1. An instrument for measuring the concentration of particulates in a fluid, including:
    particulate collecting means for collecting the particulates in the fluid;
    temperature measuring means for measuring the temperature of the particulate collecting means;
    flow rate measuring means for measuring a flow rate of the fluid passing through the particulate collecting means;
    impedance measuring means for measuring the impedance of the particulate collecting means; and
    information processing means,
    wherein the information processing means includes:
    time measuring means for measuring the elapse of time;
    constant determining means for determining an impedance change per unit time-particulate concentration constant from the measured temperature and the measured flow rate;
    impedance change per unit time computing means for computing a change of the measured impedance per unit time measured by the time measuring means; and
    particulate concentration determining means for determining the concentration of the particulates from the change of the impedance per unit time computed by the impedance change per unit time computing means by use of the impedance change per unit time-particulate concentration constant determined by the constant determining means.

2. A method for measuring the concentration of particulates in a fluid, including the steps of:
    measuring the temperature, a flow rate and the impedance of particulate collecting means for collecting the particulates in the fluid;
    determining an impedance change per unit time-particulate concentration constant from the measured temperature and flow rate;
    computing a change of the measured impedance per unit time; and
    determining the concentration of the particulates from the computed change of the impedance per unit time by use of the determined impedance change per unit time-particulate concentration constant.

3. A non-transitory computer-readable medium containing a set of instructions that cause a computer to perform a process for measuring the concentration of particulates in a fluid, the process comprising:
    accepting an input of temperature, flow rate and impedance;
    determining an impedance change per unit time-particulate concentration constant from the accepted temperature and flow rate;
    computing a change of the input impedance per unit time; and
    determining the concentration of the particulates from the computed change of the impedance per unit time by use of the determined impedance change per unit time-particulate concentration constant.

* * * * *